(12) United States Patent
Angeloni Suter et al.

(10) Patent No.: US 9,371,508 B2
(45) Date of Patent: Jun. 21, 2016

(54) CLAMPING INSERT FOR CELL CULTURE

(75) Inventors: Silvia Angeloni Suter, Saint-Blaise (CH); Martha Liley, Saint-Blaise (CH)

(73) Assignee: CSEM CENTRE SUISSE D'ELECTRONIQUE ET DE MICROTECHNIQUE SA, RECHERCHE ET DEVELOPPEMENT, Neuchatel (CH)

( * ) Notice: Subject to any disclaimer, the term of this patent is extended or adjusted under 35 U.S.C. 154(b) by 0 days.

(21) Appl. No.: 13/554,370

(22) Filed: Jul. 20, 2012

(65) Prior Publication Data
US 2013/0022500 A1    Jan. 24, 2013

(30) Foreign Application Priority Data

Jul. 21, 2011  (EP) ..................................... 11174937

(51) Int. Cl.
| | |
|---|---|
| *C12M 1/34* | (2006.01) |
| *C12M 3/00* | (2006.01) |
| *C12M 1/12* | (2006.01) |
| *C12M 1/00* | (2006.01) |

(52) U.S. Cl.
CPC ............... *C12M 25/04* (2013.01); *C12M 23/00* (2013.01); *C12M 25/08* (2013.01); *Y10T 29/49998* (2015.01)

(58) Field of Classification Search
CPC ...... C12M 23/34; C12M 25/04; C12M 25/08; B01L 3/50825; B01L 3/50853
USPC ........... 435/283.1, 287.1, 288.3, 288.4, 288.5
See application file for complete search history.

(56) References Cited

U.S. PATENT DOCUMENTS

| | | | |
|---|---|---|---|
| 4,812,407 A | * | 3/1989 | Buchmann et al. ........ 435/287.9 |
| 5,104,804 A | | 4/1992 | Humphries et al. |

(Continued)

FOREIGN PATENT DOCUMENTS

| | | |
|---|---|---|
| EP | 0 239 697 A2 | 10/1987 |
| EP | 1 416 042 A1 | 5/2004 |
| WO | WO 2012/045368 * | 4/2012 |

OTHER PUBLICATIONS

Ma, Sarina Harris, et al., An endothelial and astrocyte co-culture model of the blood-brain barrier utilizing an ultra-thin, nanofabricated silicon nitride membrane, Lab Chip, vol. 5, pp. 74-85, 2005.*

(Continued)

*Primary Examiner* — Nathan Bowers
*Assistant Examiner* — Timothy Barlow
(74) *Attorney, Agent, or Firm* — Young & Thompson

(57) ABSTRACT

A clamping insert for cell culture having a lower support with a hollow member engagable in a well of a microplate, the hollow member being open at both ends and including a support surface at one end, and first tightening elements. The clamping insert further having an inner holder sized to be fitted inside the hollow member, and second tightening elements arranged to cooperate with the first tightening elements of the hollow member to tighten reversibly between the inner holder and the support surface of the lower support a porous substrate. The inner holder further including an open channel keeping free the porous substrate. Retaining elements intended to cooperate with the well of the microplate are provided to allow the clamping insert to be suspended in the well, and sealing elements are provided to hermetically seal the contact area between the clamping insert and the porous substrate.

20 Claims, 5 Drawing Sheets

(56) References Cited

U.S. PATENT DOCUMENTS

| | | | |
|---|---|---|---|
| 5,139,951 A | 8/1992 | Butz et al. | |
| 5,358,690 A * | 10/1994 | Guirguis | 435/288.1 |
| 5,591,636 A * | 1/1997 | Grass | 435/287.1 |
| 5,652,142 A * | 7/1997 | Barker | C12M 25/04 435/297.1 |
| 5,795,775 A | 8/1998 | Lahm et al. | |
| 2002/0197631 A1 * | 12/2002 | Lawrence et al. | 435/287.2 |
| 2005/0266547 A1 * | 12/2005 | Scherze et al. | 435/287.1 |
| 2007/0231884 A1 * | 10/2007 | Kitagawa et al. | 435/289.1 |
| 2008/0009027 A1 | 1/2008 | Fraker et al. | |
| 2008/0076170 A1 | 3/2008 | Annala et al. | |

OTHER PUBLICATIONS

European Search Report, dated Dec. 2, 2011, from corresponding Europe application.

* cited by examiner

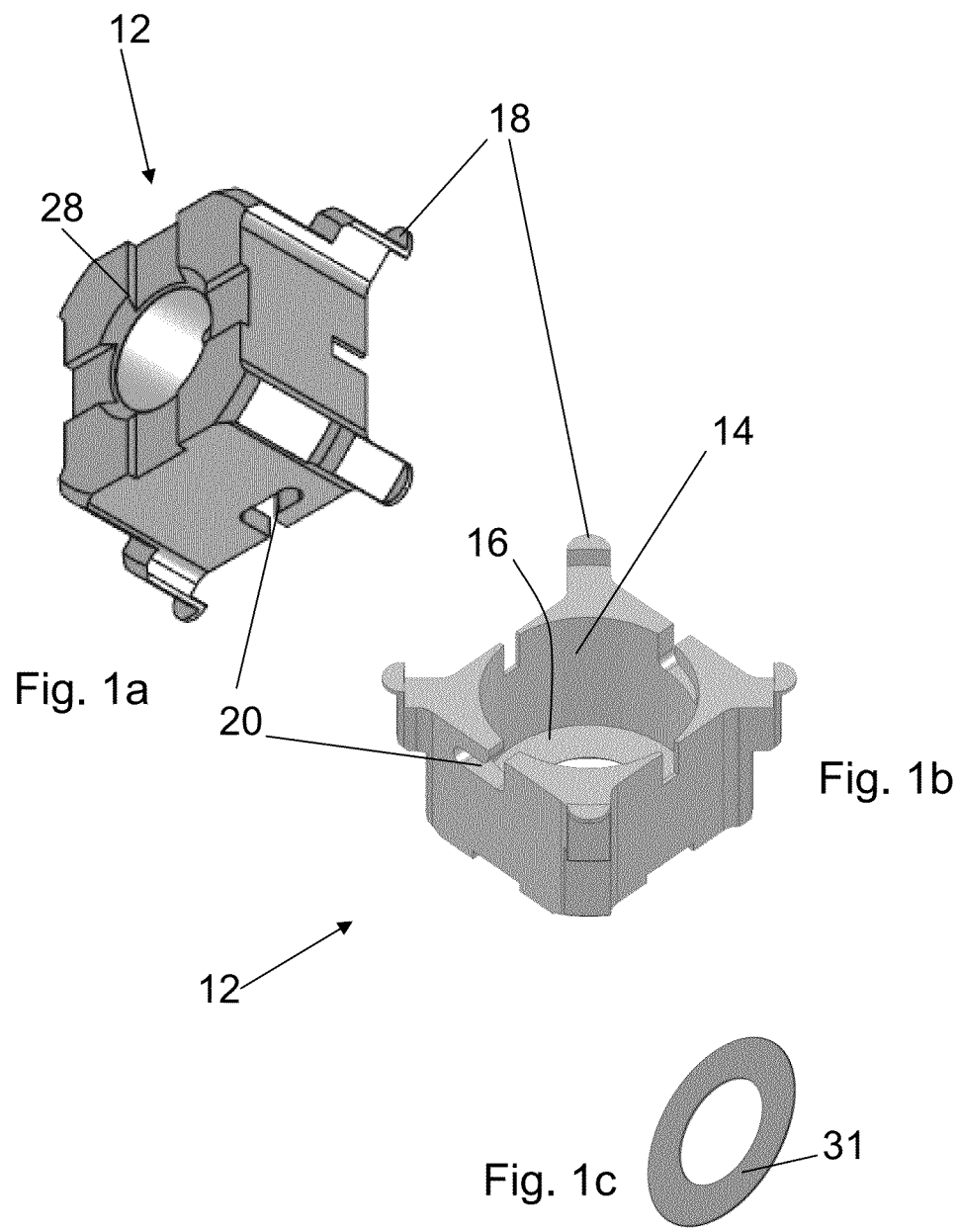

34   Fig. 4

32

CLAMPING INSERT FOR CELL CULTURE

DESCRIPTION TECHNICAL FIELD

The present invention relates to the field of cell biology and cell culture. It more particularly relates to inserts used together with microwell plates to perform various biological experiments.

STATE OF THE ART

In vitro models of biological barriers (such as lung, skin, the intestines and the blood-brain barrier) are used, for example, to screen potential pharmaceuticals and toxins for their ability to enter into and to move around the human body. In vitro models consist of a single layer or multiple layers of cells that are cultured in the laboratory so as to mimic the properties of biological barriers in the body.

The function of biological barriers in the body is to divide the inside of the body from the outside (e.g skin, lungs, the intestines) or different compartments of the body from each other (e.g. the blood-brain barrier, the walls of blood vessels). In order to model this function in the laboratory, in vitro models of biological barriers are cultured on porous membranes. This is commonly done using microporous well inserts.

The well insert is used in combination with a microwell plate consisting of a number of wells made in plastic. The insert is inserted into a well, which it divides in two, a top (apical) compartment and a bottom (basolateral) compartment which communicate via a porous membrane at the bottom of the insert. Cells are added to the apical side of the well insert and are cultured on the porous membrane. Typically, the cells will grow to form a watertight layer that divides the apical from the basolateral compartment, as in the body.

The porous membrane is usually made of polymers or of inorganic aluminium oxide. It is welded, moulded or glued to the wall of the insert, so as to obtain a perfect seal. Indeed, it is necessary that the exchanges of material between apical and basolateral compartments take place only through the microporous membrane and the cell layer upon it. The membrane and the insert form a disposable assembly.

To study, for example, pharmaceutical drug transport or permeation across the model biological barrier, candidate drugs are added to the apical compartment, which represents the outside of the body for a skin model, or the inside of the lungs, or of the intestines, etc. . . . . Permeation is quantified by measuring the concentration of the candidate drug in the basolateral compartment, which represents the inside of the body, after a fixed time.

Recently, a new type of porous substrate has been developed using microfabrication technology. Such substrates are fabricated by first depositing a thin layer of ceramic material, such as $Si_3N_4$, on a silicon wafer. Pores are then etched in the $Si_3N_4$ by photolithography followed by a dry etch. The silicon wafer is then etched from the other side to remove the entire thickness of silicon in selected areas, leaving a set of supports for the transparent porous substrate that remain after removal of the silicon. The resulting porous substrate comprises a silicon nitride membrane supported on a silicon frame which gives it suitable mechanical properties. Thus, this kind of substrate is rigid.

Some advantageous of this type of porous substrates in comparison with other membranes, are listed hereafter:

much thinner membranes (less than 1 micrometer thick) can be fabricated, namely at least 20 times thinner than the commonly-used membranes in commercial well inserts;
pore sizes, shapes, densities and distributions in the membrane can be tuned as desired;
the membrane is highly transparent in both air and water independently of the pore size and density;
the membranes are resistant to acids, bases, solvents, high temperatures and e-beam exposure;
the membranes are reusable (reconditionable) after cell culture.

These properties are available advantageously in one unique combination together with the properties commonly exhibited by the existing membranes such as:
low intrinsic fluorescence of the membrane;
possible chemical pretreatment to enhance cell culture
good cell growth in general and, in particular, the formation of tight layers of epithelial cells;
they withstand common sterilization procedures.

However, this kind of rigid substrate presents two major drawbacks. Firstly, it is more expensive than the commonly used polymer microporous substrates. This can be overcome by its reuse. In addition, it requires a specific holder that makes it compatible with a commercial well plate and also with routine laboratory practice.

A cell culture insert has been proposed in US2008076170. Such insert includes a body having a grip extending sideways from the body and a locking ring adapted to be fitted around the body. The cell culture insert is kept in place by friction contact against interior sidewalls of a cavity of a cell culture vessel. Its height position can be adjusted inside said cavity.

However, the insert as disclosed may only be used with a flexible membrane, able to be folded between the locking ring and the body. Such an embodiment does not define a tight seal but allows culture medium to circulate from one side of the membrane to another without crossing through the membrane, but by gaps occurring between the membrane and the body or between the membrane and the locking ring. Therefore, this clamped membrane, because of these gaps, does not define two reaction chambers with exclusive exchange of solvent and solutes through the membrane itself. Therefore the taught insert cannot be used to investigate transport properties through model biological barriers. Moreover, conventional sealing means can not be directly implemented, since it may not be compatible with a sliding engagement of the locking ring on the body.

Thus, the present invention aims to alleviate these problems and allow a practical use of this type of rigid substrate.

SUMMARY OF THE INVENTION

To this end, the invention concerns a clamping insert for cell culture comprising:
a lower support comprising:
  i. a hollow member sized to be engaged in a well of a microplate, said hollow member being open at its both ends and comprising a support surface at one of its ends,
  ii. first tightening means,
an inner holder sized to be fitted inside the hollow member, and comprising second tightening means arranged to cooperate with said first tightening means of the hollow member to tighten reversibly between the inner holder and the support surface of the lower support a porous substrate, said inner holder comprising an open channel keeping free the porous substrate;

retaining means intended to cooperate with the well of the microplate to allow the clamping insert to be suspended in the well of the microplate, sealing means to hermetically seal the contact area between the inner holder and said porous substrate.

Some other advantageous characteristics are specified in the claims.

The invention also concerns an assembly comprising such a clamping insert and a porous substrate. The invention also concerns a method for clamping a porous substrate with such an insert. Said method comprises the following steps:

unfitting the inner holder and the lower support, placing said porous substrate on the support surface of the lower insert, disposing the inner holder so as to clamp the porous substrate between the inner holder and the lower support, tightening the inner holder in the lower support.

A dedicated tool comprising some driving structures intended to cooperate with corresponding structures arranged in the inner holder may be used for the tightening step if appropriate.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIGS. 1a and 1b are two perspective views of an embodiment of the lower support, FIG. 1c represents an anti-wear ring intended to cooperate with the lower support.

DETAILED DESCRIPTION

Figure 2A:
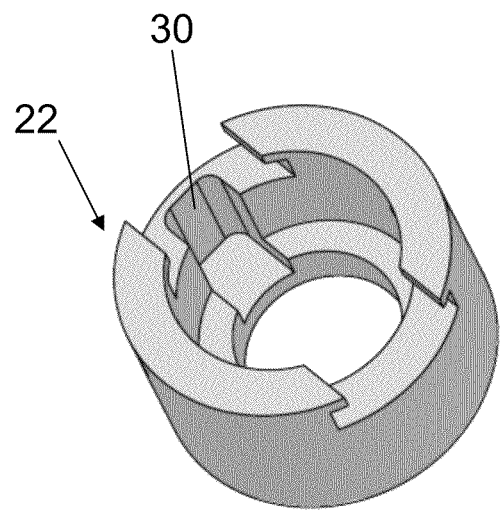
FIGS. 2a and 2b are two perspective views of an embodiment of the inner holder.
Figure 2B:
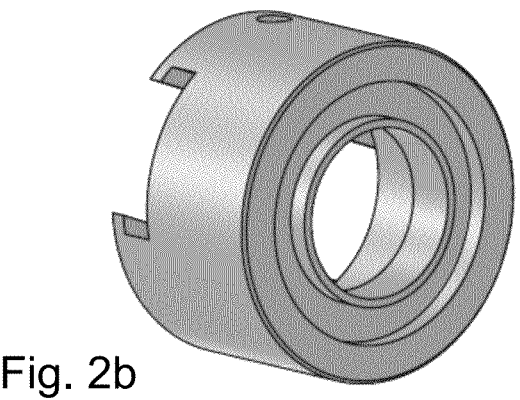
Figure 2C:
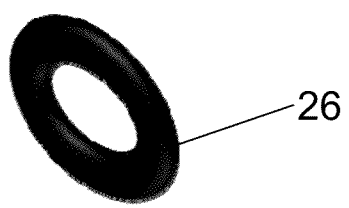
FIG. 2c represents a seal intended to cooperate with the inner holder.
Figure 3:
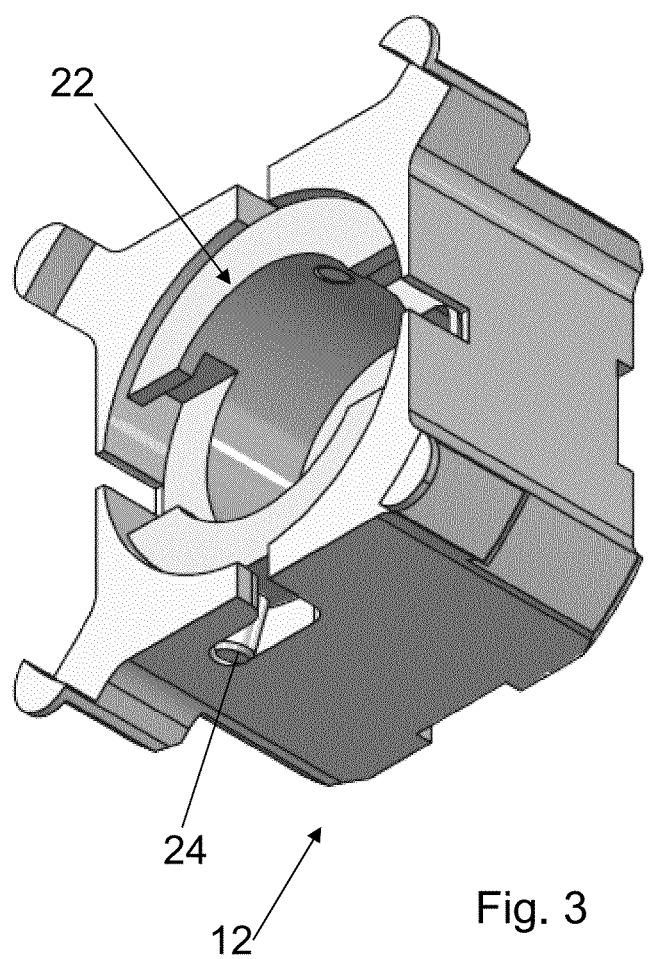
FIG. 3 show the assembled clamping insert according one embodiment of the invention.

FIGS. 1, 2 and 3 represent a preferred embodiment of an insert according to the invention. This insert aims to facilitate the use as a biological substrate of a porous substrate made with a $Si_3N_4$ layer deposited on a silicon wafer and then micromachined. Such a porous substrate 10 can be seen on FIGS. 5 and 6. This substrate as such is not part of the invention and will not be described in detail. One can refer to Madou, M. J, *Fundamental of Microfabrication*: the science of miniaturization, Second Edition, CRC Press 2002, for more information about this technology. It should be noted that such substrates are rigid.

It should be noticed that, due to specifications and costs of the substrate, it should preferably be arranged in a reusable way.

Thus, to this end, the insert according to the invention comprises a lower support 12 (FIGS. 1a and 1b) comprising a hollow member 14 sized to be engaged in a well of a microplate, preferably of a standard microplate. The hollow member 14 could be made in different suitable materials, like plastic or aluminium. PEEK (polyether ether ketone), PC (polycarbonate), polystyrene or similar polymers are well suited since they resist typical sterilization conditions and they can be injection moulded in a low-cost production process.

The hollow member 14 is open at both its ends. At one end, its wall defines a reverse side which forms a support surface 16 for the porous substrate 10. The lower support 12 furthermore comprises some flanges 18 extending from the wall of the hollow member 14 oppositely to the end comprising said support surface 16. These flanges 18 define retaining means. They are sized and arranged so as to allow the lower support 12 and the whole insert to rest on the sides of the microplate well and so as to avoid the whole assembly touching the bottom of the microplate well.

The lower support 12 furthermore comprises first tightening means. In the detailed example, these first tightening means take shape of two grooves 20, diametrically opposed. Each groove 20 comprises a first longitudinal part, parallel to the longitudinal axis of the cylinder of the hollow member 14. This first longitudinal part is extended by a second inclined part, essentially perpendicular to the longitudinal axis but with a slight slope directed toward the support surface 16.

The insert according to the invention comprises furthermore an inner holder 22 (FIGS. 2a and 2b) sized to be adjusted inside the hollow member 14. More precisely, the inner holder 22 is similar to the hollow member 14, the exterior dimension of which being slightly lower than the interior dimensions of the hollow member 14. In this example, the inner holder 22 has a cylindrical shape. This inner holder 22 can be made of plastic, especially PEEK (polyether ether ketone), PC (polycarbonate), polystyrene or the like.

The inner holder 22 comprises second tightening means arranged to cooperate with the first tightening means. In this example, said second tightening means are two pins 24 diametrically opposed and sized to be engaged in the grooves 20 of the hollow member 14, so as to form a bayonet fitting. The pins 24 and grooves 20 could also be disposed reversely. A torque limiting system could be implemented so as to avoid damaging the porous substrate.

The length of the inner holder 22 is sized so that, when the inner holder 22 is tightened on the lower support 12, a porous substrate 10 may be clamped between both of them.

Thus, there may remain a free space between the support surface 16 and the end of the inner holder 22, with a height lower than the thickness of the porous substrate. When present, the porous substrate is held firmly in this free space. To decrease the pressure and/or improve the clamping, interfaces can be fitted with suitable coatings in rubber, Teflon or other elastic materials which will also reduce wear.

As explained above, it is of utmost importance that apical and basolateral compartments be well separated so that exchanges between them be only implemented through the substrate and the cells grown on it.

Figure 5:
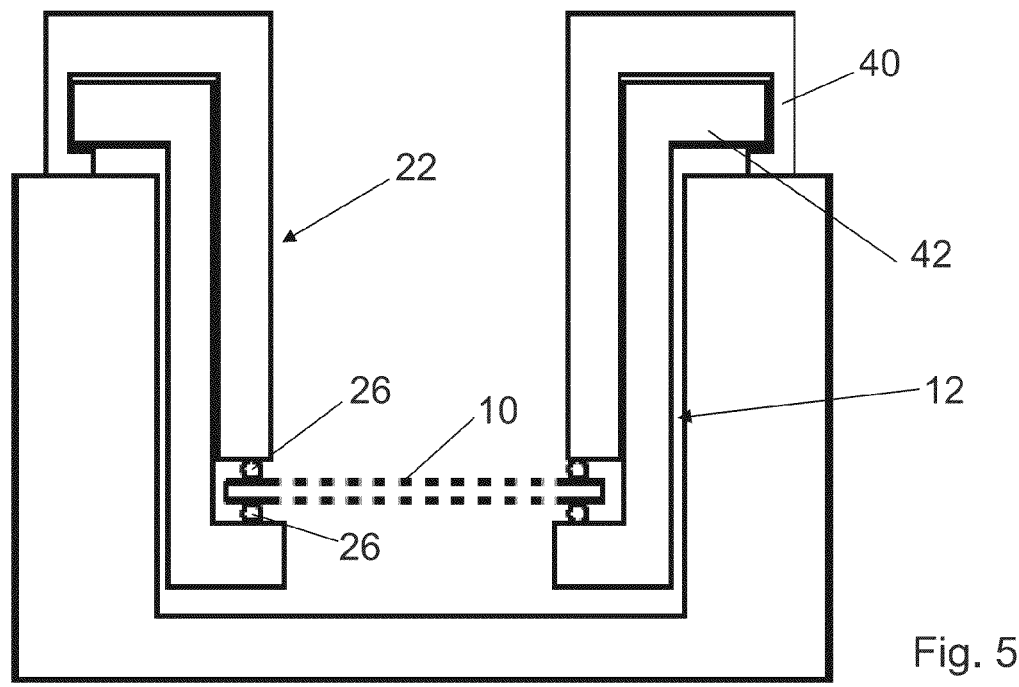
FIGS. 5 and 6 propose sketches of two other embodiments of the invention.
Figure 6:
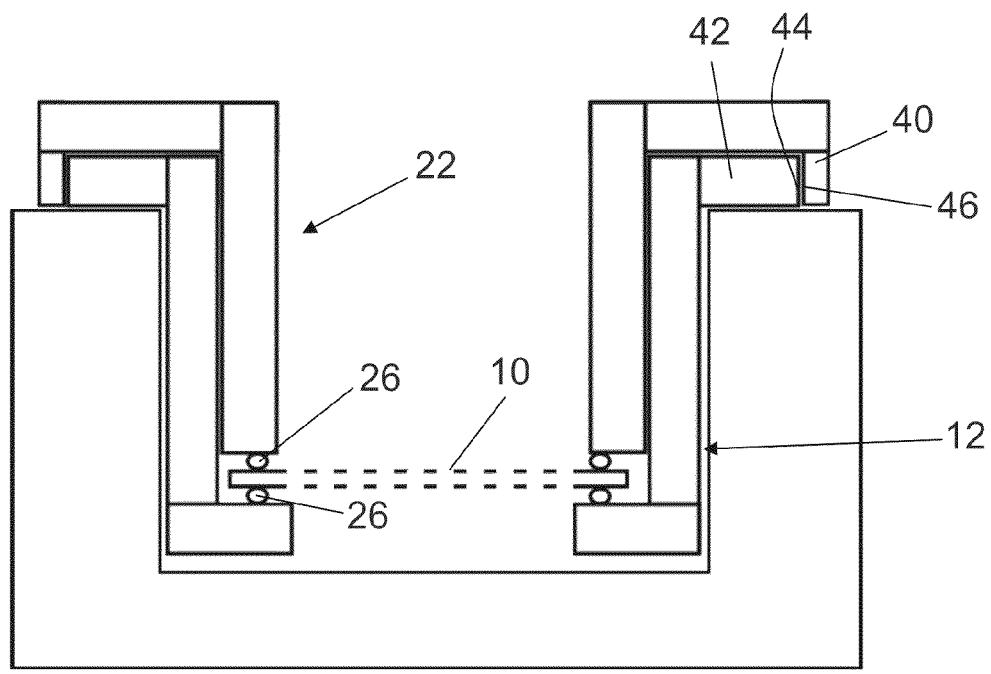

For this purpose and according an advantageous aspect of the invention, the insert includes a sealing means to hermetically seal the contact area between the inner holder 22 and said porous substrate. One could also consider disposing the seal 26 between the substrate end the lower support 12. FIGS. 5 and 6 show that it is possible to dispose two seals, one on each side of the porous substrate 10.

For example, sealing means may be implemented with a silicone ring 26 (FIG. 2c) interposed between the inner holder 22 and the porous substrate 10. Other suitable materials may be used for the seal 26, like rubber or elastic polymers.

An annular recess may be also engraved in the substrate, in which the seal may take place. Thus, the seal 26 is perfectly positioned and the tightness area is perfectly defined around the porous membrane and the culture zone.

The insert according to the invention may also present some interesting and advantageous features.

For instance, the lower support 12 may comprise grooves 28 to allow easy release of air bubbles from below the porous membrane.

The inner wall of the inner holder 22 may also comprise a guiding groove 30 oriented longitudinally, for both pipetting and TEER (Trans Epithelial Electrical Resistance) electrodes. The guiding groove 30 may guide the tip of a pipette up to 1 mm above the porous substrate 10 without touching the cell culture and membrane damaging. The same groove 30 can be used to easily position reproducibly the electrodes used to record TEER values.

As mentioned above, the support surface 16 of the lower support 12 may be equipped with some antiwear means. For example, it may be coated with a suitable antiwear coating or comprise an antiwear ring 31 (FIG. 1c). Teflon or other low friction polymers are well suited as antiwear means.

Figure 4:
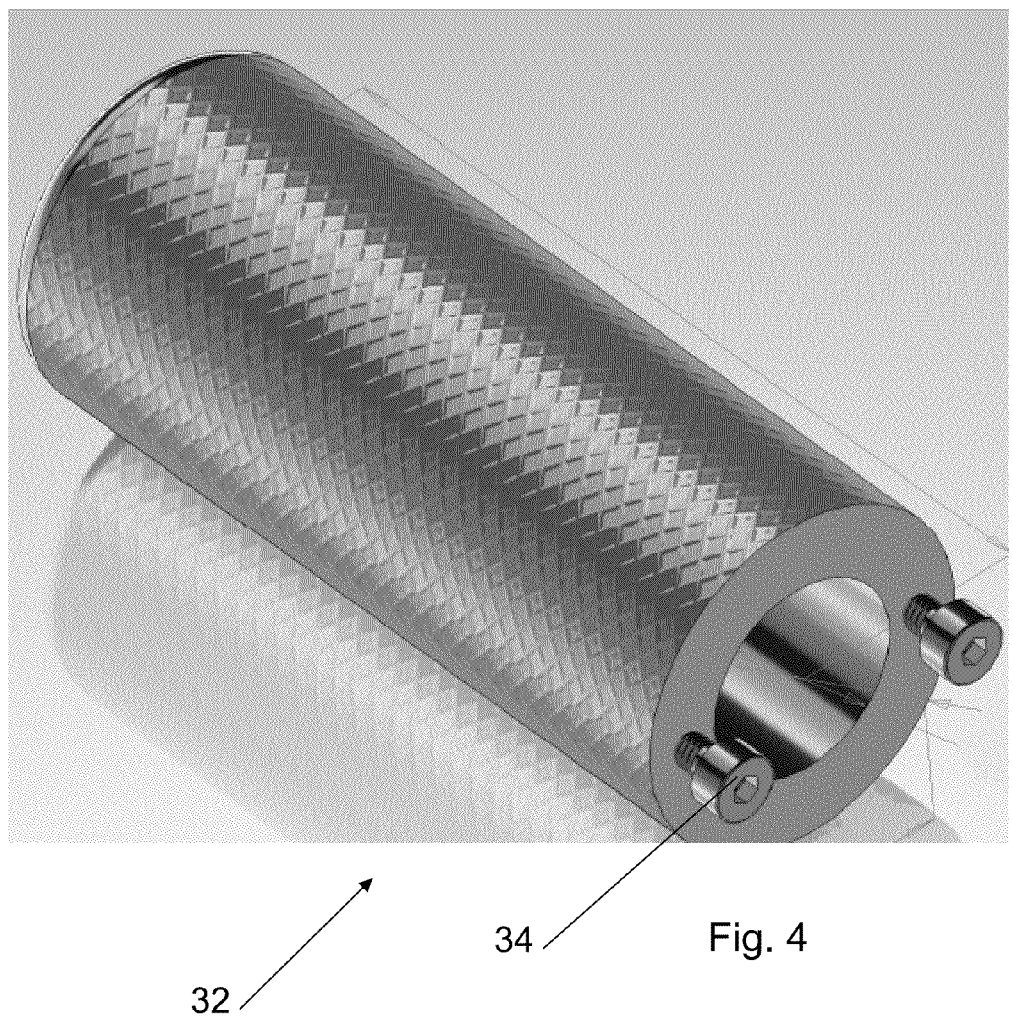
FIG. 4 represents an example of an assembling/disassembling tool adapted to the invention.

To enhance the use of the insert according to the invention, FIG. 4 also proposes a tool 32 designed to assemble/disassemble easily the inner holder 22 on the lower support 12, reducing any risk of contamination or of wrong manipulation. Such tool 32 comprises a grip to be handled by a user or by a robot. Said tool 32 also comprises some driving structures 34 able to cooperate with corresponding structures arranged in the inner holder 22. Once the driving structures 34 are engaged with the corresponding structures of the inner holder 22, one can tighten/untighten the inner holder 22 in the lower support 12 by rotating the tool 32 in one or in the other direction, while the lower support 12 is fixed. As shown in FIG. 4, the driving structure may be obtained by screws or pins, while the corresponding structure may be obtained by grooves realized on the top end of the inner holder 22. One can implement a torque limiting system in the tool grip or between the grip and the driving structure, to avoid damaging the substrate.

Other tightening means could also be considered. For example, FIG. 5 proposes to assembly the inner holder 22 by clipping it on the lower support 12. To this end, the inner holder 22 may comprise some elastic extensions 40, sized and shaped to hook a rim 42 or the flanges of the lower support 12. The elastic properties of the extensions allow, when the inner holder is hooked, to fix rigidly these two parts and to clamp the porous substrate in between. The elastic properties allow however to unclip these two parts.

FIG. 6 proposes to assembly the inner holder 22 by screwing it on the lower support 12. Similarly to the embodiment of FIG. 5, the inner holder 22 may comprise some extensions 40, comprising first screwing means 44 (i.e. thread or tapping), sized and shaped to cooperate with second screwing means 46 (respectively tapping or thread) of a rim 42 of the lower support 12. These two parts can be screwed in order to clamp the porous substrate in between.

Thus, the insert according to the invention allows clamping a porous substrate 10 comprising a silicon nitride membrane supported on a silicon frame and obtained by microfabrication, in an efficient and practical way. The holder is key to the use of the porous substrate, the design of which can be tuned according to the most precise requirements of the cell culture. One can therefore benefit from the advantages of such a substrate, as detailed in the introduction. Indeed, despite the very tight seal, the substrate can easily be removed after an experiment and can be reconditioned, i.e. cleaned to obtain a bare porous substrate 10 and reused for a subsequent cell culture. Furthermore, the assembling and disassembling procedure allows the membrane to be turned upside down and still incubated with the physiological buffer. These properties may improve the co-culture procedure. As explained above, the insert is well suited for TEER measurements.

In a further improvement of the insert according to the invention, one could consider integrating the relevant contact pads and circuits for TEER measurements. For example, thanks to its silicon basis, the substrate could be provided with integrated electrodes. The insert could also be equipped with contact pads designed to facilitate electrical contact with the external equipment. This would greatly improve the reproducibility of electrical measurements.

In another improvement of the insert, one could consider integrating a wave guide in the inner holder 22, such wave guide being used to bring the light close the surface bearing the culture cell, either for growth improvement or the illumination for optical inspection or for preculture UV sterilization.

The examples above should not be considered as limiting. Those skilled in the art will appreciate that numerous modifications can be made thereof without departing from its spirit. The clamping insert according to the invention can be used for any kind of rigid substrates. The scope of the invention is to be determined by the appended claims and their equivalent.

What is claimed is:

1. A clamping insert for cell culture comprising:
   a lower support (12) comprising:
   i. a hollow member sized to be engaged in a well of a microplate, said hollow member having an upper end with a first opening, a lower end with a second opening, an interior wall extending between the first and second openings and defining a open channel therebetween, and a support surface at lower end, said support surface extending inwardly from the interior wall and including a central opening so as to defining an open passage between an uppermost surface of the hollow member and a lowermost surface of the hollow member, and
   ii. a first retaining element comprised of a flanges (42) extending, at the upper end, outwardly from an outside wall of the hollow member oppositely to the lower end comprising said support surface, the flanges (42) having an outermost outward-facing surface with a first threaded screwing element (44), wherein said first retaining element is adapted to cooperate with an upper surface of the well of the microplate to allow the hollow member a) to be suspended in the well of the microplate, via a lower surface of the first retaining element resting on the upper surface of the well of the microplate, and b) to divide the well of the microplate into an apical compartment and a basolateral compartment in communication via a porous substrate;
   an inner holder (22) sized to be fitted inside the open channel of the hollow member, and comprising a lowermost surface and a second retaining element (42, 44) that cooperates with said first retaining element of the hollow member to clamp reversibly said porous substrate between the lowermost surface of the inner holder and the support surface of the lower support, said inner holder comprising an open channel extending from an uppermost surface of the inner holder to the lowermost surface of the inner holder and arranged to provide access to the porous substrate,
   wherein said second retaining element is comprised of a second threaded screwing element (46) that co-operates with the first threaded screwing element (44) located on the outermost outward-facing surface of the outermost edge portion of the flanges (42) to screw together the inner holder and the lower support to thereby form a screw fitting; and a seal, that when placed in contact with said porous substrate, hermetically seals a contact area between said porous substrate and one of a group consisting of the inner holder and the lower support.

2. The clamping insert of claim 1, wherein an inner wall of the inner holder also comprises a guiding groove oriented longitudinally, allowing passage of a pipette.

3. The clamping insert of claim 2, wherein said seal is interposed between the inner holder and the porous substrate and/or interposed between the porous substrate and the lower support.

4. The clamping insert of claim 1, wherein an inner wall of the inner holder also comprises a guiding groove oriented longitudinally, allowing passage of a Trans Epithelial Electrical Resistance (TEER) electrode.

5. The clamping insert of claim 4, wherein said seal is interposed between the inner holder and the porous substrate and/or interposed between the porous substrate and the lower support.

6. The clamping insert of claim 1, wherein said seal is interposed between the inner holder and the porous substrate and/or interposed between the porous substrate and the lower support.

7. The clamping insert of claim 1, wherein the inner holder is made of one of the group consisting of PEEK, polycarbonate, polystyrene, and another plastic compatible with cell culture.

8. The clamping insert of claim 1, wherein the lower support is made of one of the group consisting of PEEK, polycarbonate, polystyrene, and another plastic compatible with cell culture.

9. The clamping insert of claim 1, wherein the inner holder and the lower support are made of one of the group consisting of PEEK, polycarbonate, polystyrene, and another plastic compatible with cell culture.

10. The clamping insert according to claim 1, wherein the inner holder is situated entirely within the open channel of the hollow member.

11. A clamping insert for cell culture comprising:
a lower support (12) comprising:
i. a hollow member sized to be engaged in a well of a microplate, said hollow member having an upper end with a first opening, a lower end with a second opening, an interior wall extending between the first and second openings and defining a open channel therebetween, and a support surface at lower end, said support surface extending inwardly from the interior wall and including a central opening so as to defining an open passage between an uppermost surface of the hollow member and a lowermost surface of the hollow member, and
ii. a first retaining element comprised of a flanges (42) extending, at the upper end, outwardly from an outside wall of the hollow member oppositely to the lower end comprising said support surface, the flanges (42) having an outermost outward-facing surface and an outermost edge portion with a lower surface, wherein said first retaining element is adapted to cooperate with an upper surface of the well of the microplate to allow the hollow member a) to be suspended in the well of the microplate, via a lower surface of the first retaining element resting on the upper surface of the well of the microplate, and b) to divide the well of the microplate into an apical compartment and a basolateral compartment in communication via a porous substrate;

an inner holder (22) sized to be fitted inside the open channel of the hollow member, and comprising a lowermost surface and a second retaining element (42, 44) that cooperates with said first retaining element of the hollow member to clamp reversibly said porous substrate between the lowermost surface of the inner holder and the support surface of the lower support, said inner holder comprising an open channel extending from an uppermost surface of the inner holder to the lowermost surface of the inner holder and arranged to provide access to the porous substrate, wherein said second retaining element is comprised of elastic extensions (40) sized and shaped to hook the outermost outward-facing surface and the lower surface of the outermost edge portion of the flanges (42), to form a clipping fitting; and a seal, that when placed in contact with said porous substrate, hermetically seals a contact area between said porous substrate and one of a group consisting of the inner holder and the lower support.

12. The clamping insert of claim 11, wherein an inner wall of the inner holder also comprises a guiding groove oriented longitudinally, allowing passage of a pipette.

13. The clamping insert of claim 12, wherein said seal is interposed between the inner holder and the porous substrate and/or interposed between the porous substrate and the lower support.

14. The clamping insert of claim 11, wherein an inner wall of the inner holder also comprises a guiding groove oriented longitudinally, allowing passage of a Trans Epithelial Electrical Resistance (TEER) electrode.

15. The clamping insert of claim 14, wherein said seal is interposed between the inner holder and the porous substrate and/or interposed between the porous substrate and the lower support.

16. The clamping insert of claim 11, wherein said seal is interposed between the inner holder and the porous substrate and/or interposed between the porous substrate and the lower support.

17. The clamping insert of claim 11, wherein the inner holder is made of one of the group consisting of PEEK, polycarbonate, polystyrene, and another plastic compatible with cell culture.

18. The clamping insert of claim 11, wherein the lower support is made of one of the group consisting of PEEK, polycarbonate, polystyrene, and another plastic compatible with cell culture.

19. The clamping insert of claim 11, wherein the inner holder and the lower support are made of one of the group consisting of PEEK, polycarbonate, polystyrene, and another plastic compatible with cell culture.

20. The clamping insert according to claim 11, wherein the inner holder is situated entirely within the open channel of the hollow member.

\* \* \* \* \*